US011970690B2

United States Patent
Farrell et al.

(10) Patent No.: US 11,970,690 B2
(45) Date of Patent: Apr. 30, 2024

(54) **METHODS OF CULTIVATING *BORDETELLA* SPECIES**

(71) Applicant: SANOFI PASTEUR INC., Swiftwater, PA (US)

(72) Inventors: Patrick Farrell, Holland Landing (CA); Bo Zhi Sun, Waterdown (CA); Fabien Barbirato, Brignais (FR); Javier de Jesus Menendez Diaz, Pickering (CA); Andrew Chiappetta, Vaughan (CA)

(73) Assignee: SANOFI PASTEUR INC., Swiftwater, PA (US)

( * ) Notice: Subject to any disclaimer, the term of this patent is extended or adjusted under 35 U.S.C. 154(b) by 720 days.

(21) Appl. No.: 16/981,200

(22) PCT Filed: Mar. 19, 2019

(86) PCT No.: PCT/IB2019/000305
§ 371 (c)(1),
(2) Date: Sep. 15, 2020

(87) PCT Pub. No.: WO2019/180507
PCT Pub. Date: Sep. 26, 2019

(65) Prior Publication Data
US 2020/0407678 A1    Dec. 31, 2020

Related U.S. Application Data

(60) Provisional application No. 62/645,473, filed on Mar. 20, 2018.

(51) Int. Cl.
| | | |
|---|---|---|
| *C12N 1/20* | (2006.01) | |
| *A61K 39/02* | (2006.01) | |
| *C12N 1/38* | (2006.01) | |

(52) U.S. Cl.
CPC ............ *C12N 1/20* (2013.01); *A61K 39/099* (2013.01); *C12N 1/38* (2013.01); *C12N 2500/02* (2013.01);
(Continued)

(58) Field of Classification Search
CPC ........ C12N 1/20; C12N 1/38; C12N 2500/02; C12N 2500/34; C12N 2500/60; C12N 2500/72; A61K 39/099
See application file for complete search history.

(56) References Cited

FOREIGN PATENT DOCUMENTS

| EP | 0427462 | 5/1991 | |
|---|---|---|---|
| EP | 0659879 A2 * | 6/1995 | ............... C12N 1/20 |
| EP | 0659879 A2 | 6/1995 | |

OTHER PUBLICATIONS

Fingermann et al. "Acid tolerance response of Bordetella bronchiseptica in avirulent phase", Sep. 5, 2015, Microbiological Research, vol. 181, p. 52-60. (Year: 2015).*
(Continued)

*Primary Examiner* — Gary B Nickol
*Assistant Examiner* — Amelia Nicole Dickens
(74) *Attorney, Agent, or Firm* — MH2 TECHNOLOGY LAW GROUP, LLP

(57) ABSTRACT

The present disclosure is directed to a method for cultivating a *Bordetella* species, comprising: cultivating a *Bordetella* species under aerobic conditions in a liquid culture medium; and maintaining a pH of the liquid culture medium by using a strong acid, such as nitric acid, or using a first and second acid, wherein the first acid is an inorganic acid that dissociates essentially completely in water, such as nitric acid, hydrochloric acid or sulfuric acid, and wherein the second acid is an inorganic acid having an acid dissociation constant (pKa) of greater than 1, such as phosphoric acid. Methods for increasing the yield of *Bordetella* fimbrial agglutinogen
(Continued)

2 and fimbrial agglutinogen 3 (FIM2/3) in a supernatant fraction from a *Bordetella* culture are also provided.

17 Claims, 6 Drawing Sheets

(52) U.S. Cl.
 CPC ...... *C12N 2500/34* (2013.01); *C12N 2500/60* (2013.01); *C12N 2500/72* (2013.01)

(56) References Cited

OTHER PUBLICATIONS

Frolich et al. Improved pertussis toxin production by Bordetella pertussis through adjusting the growth medium's ionic composition, 1995, Journal of Biotechnology, vol. 39, p. 205-219. (Year: 1995).*

Licari et al. "The effect of pH on the production of pertussis toxin by Bordetella pertussis", 1991, Journal of Biotechnology, vol. 17, p. 189-193. (Year: 1991).*
Partial European Search Report dated Nov. 26, 2021 for corresponding European Application No. 19771590.7, 10 pages.
International Search Report and Written Opinion dated Aug. 15, 2019 from International Application No. PCT/IB2019/000305 (Authorized Officer, Brad Temple), 11 Pages.
Licari et al., "The effect of pH on the production of pertussis toxin by Bordetella pertussis", Journal of Biotechnology, 1991, vol. 17, No. 2, pp. 189-193.
Office Action dated Feb. 7, 2023 for corresponding Japanese Application No. 2020-550857, 13 pages including English translation.
Japanese Journal of Bacteriology, 1996, vol. 51, No. 3, pp. 737-744 (See p. 4 (paragraph 4) of the translation of Japanese Office Action dated Feb. 7, 2023 for a concise explanation of the relevance of this document, which is referred to as D2 in the Office Action).

* cited by examiner

METHODS OF CULTIVATING *BORDETELLA* SPECIES

CROSS-REFERENCE TO RELATED APPLICATIONS

This application is a U.S. National Stage application of PCT/IB2019/000305 filed 19 Mar. 2019, which claims the benefit of, and relies on the filing date of, U.S. provisional patent application No. 62/645,473, filed 20 Mar. 2018, the entire disclosure of which is herein incorporated by reference.

TECHNICAL FIELD

This application relates generally to methods for cultivating *Bordetella* species, such as *Bordetella pertussis*.

BACKGROUND

Whooping cough is a bacterial infection of the lungs characterized by severe coughing fits. *Bordetella pertussis* is the major causative agent of this condition. Vaccines have been available for decades comprising killed whole cells of *B. pertussis* (wP) that are chemically detoxified and formulated with Diphtheria and Tetanus antigens. Since the 1990s, wP vaccines have been replaced in many countries by acellular pertussis vaccines. Acellular pertussis (aP) vaccines induce relatively fewer side-effects compared to wP vaccines, which are associated with a high risk for fever, reactogenicity at the injection site and, to a lesser extent, convulsions.

Current acellular vaccines are based on the following virulence factors: pertussis toxin (PT), filamentous hemagglutinin (FHA), pertactin (PRN), fimbrial agglutinogen 2 and fimbrial agglutinogen 3 (FIM2/3 or FIM). While some acellular vaccines contain only PT and FHA or PT alone, it is generally believed that acellular pertussis vaccines containing PT, FHA, PRN, fimbrial agglutinogen 2 and fimbrial agglutinogen 3 components are the most effective aP vaccines currently available.

Art-known manufacturing processes for whooping cough aP vaccines are mainly composed of two phases: an upstream fermentation process and a downstream purification process. The upstream fermentation process typically involves cultivation of *Bordetella* in a series of bioreactors of increasing volume where the microorganism is grown under controlled conditions. Typically, the controlled conditions of *Bordetella* cultivation include a medium containing amino acids as an energy source. Cultivation of *Bordetella* cells is unusual in that the cells are unable to efficiently utilize certain energy sources, such as, carbohydrates, lactate and intermediates of glycolysis. Instead, the organisms use amino acids as their main carbon and energy source, typically, glutamic acid. In the utilization of glutamate, the α-amino group is removed and the carbon skeleton is converted to α-ketoglutarate, a metabolic intermediate. The oxidative deamination of glutamate, which is regulated by the enzyme glutamate dehydrogenase, follows the below reaction:

$$\text{Glutamate} + \text{NAD}^+ + \text{H}_2\text{O} = \text{NH}_4^+ + \text{NADH} + \text{H}^+ + \alpha\text{-ketoglutarate}$$

The deamination of amino acids by *Bordetella* results in an increase in pH during cultivation due to the reaction of ammonia to ammonium ions in the medium. Enhanced cell density can be achieved during *Bordetella* cultivation, at least in part, by continuously maintaining the pH of the culture medium. Accordingly, methods for cultivating *Bordetella* typically also include controlling the pH by adding an acid, typically phosphoric acid, to maintain the pH at less basic levels.

Following cultivation, the cells are separated from the supernatant (also known as centrate), which typically involves centrifugation of the cultivated culture resulting in cellular and supernatant fractions, and antigens of interest can be further isolated from the cellular and/or supernatant fractions, as appropriate. FIM is usually isolated from the cellular fraction, although smaller amounts of FIM can also be found in the supernatant. Conversely, PT, FHA and PRN, which are released from the cell during cultivation, are typically isolated from the supernatant. A significant portion of the PRN, however, often remains associated with the cells, and thus, is not present in the supernatant, resulting in a potential loss of antigen. Hence, there remains a need in the art for a more efficient method of *Bordetella* antigen production, particularly PRN production, which increases the amount of this antigen in the supernatant.

SUMMARY

The present inventors have developed a method for cultivating *Bordetella* that results in an increased amount of PRN in the supernatant. Surprisingly, the present inventors recognized that the amount of PRN in the supernatant is dependent, at least in part, upon the type of acid(s) used to maintain the pH during cultivation. Furthermore, the inventors surprisingly recognized that PRN can be increased in the supernatant without affecting the yield of other antigens by using specific acid blends for pH control. Moreover, the inventors discovered that the use of strong acids or acid blends does not result in any substantial variation in biomass levels. Accordingly, a simple change in the type of acid used for pH control results in minimal impact on downstream *Bordetella* antigen manufacturing processes. These and other unexpected benefits of the instant method are described herein below.

More particularly, in one aspect, the present disclosure is directed to a method for cultivating a *Bordetella* species, typically *Bordetella pertussis*, which method includes: cultivating a *Bordetella* species under aerobic conditions in a liquid culture medium; and maintaining a pH of the liquid culture medium during cultivation of the species, wherein maintaining the pH of the liquid culture medium includes: adding a strong acid, such as nitric acid, to the liquid culture medium as needed to maintain the pH of the liquid culture medium within a predetermined range of pH values during cultivation of the *Bordetella* species.

In addition, in another aspect, the present disclosure is directed to a method for increasing the yield of *Bordetella* fimbrial agglutinogen 2 and fimbrial agglutinogen 3 (FIM2/3) in a supernatant fraction from a *Bordetella* culture, which method includes: cultivating a *Bordetella* species, typically *Bordetella pertussis*, under aerobic conditions in a liquid culture medium; maintaining a pH of the liquid culture medium during cultivation of the species, wherein maintaining the pH of the liquid culture medium includes: adding an acid to the liquid culture medium as needed to maintain the pH of the liquid culture medium within a predetermined range of pH values during cultivation of the *Bordetella* species, wherein the acid includes an inorganic acid that dissociates essentially completely in water, such as nitric acid, hydrochloric acid or sulfuric acid, separating the liquid culture medium after cultivation of *Bordetella* into a cellular fraction and a supernatant fraction; and isolating FIM2/3 from the supernatant fraction.

In yet another aspect, the present disclosure is directed to a method for cultivating a species of *Bordetella*, typically *Bordetella pertussis*, which method includes: cultivating a *Bordetella* species under aerobic conditions in a liquid culture medium; and maintaining a pH of the liquid culture medium during cultivation of the species, wherein maintaining the pH of the liquid culture medium includes: adding a first and second acid to the liquid culture medium as needed to maintain the pH of the liquid culture medium within a predetermined range of pH values during cultivation of the *Bordetella* species, wherein the first acid is an inorganic acid that dissociates essentially completely in water, such as nitric acid, hydrochloric acid or sulfuric acid, most typically nitric acid, and wherein the second acid is an organic or inorganic acid having an acid dissociation constant (pKa) of greater than 1, such as phosphoric acid.

In some embodiments, the first acid and the second acid are combined in a solution, wherein the solution includes about 20% to about 75%, such as about 30% to about 50%, such as about 40%, of the first acid and about 25% to about 80%, such as about 50% to about 70%, such as about 60%, of the second acid (v/v).

In some embodiments, the methods described herein further include isolating *Bordetella* antigens from the liquid culture medium including, for example, separating the liquid culture medium after cultivation of *Bordetella* into a cellular fraction and a supernatant fraction.

In some embodiments, the methods described herein further include isolating one or more of Pertussis Toxin (PT), Filamentous Haemagglutinin (FHA) and pertactin (PRN) from the supernatant fraction, and isolating FIM2/3 from the cellular fraction and/or the supernatant.

In some embodiments, the methods described herein further include formulating the isolated *Bordetella* antigens as a subunit vaccine.

In any of the methods described herein, the predetermined range of pH values may be from 6.0 to 9.0, such as from 6.8 to 7.3.

In some embodiments, the cultivation of the *Bordetella* species according to the instant methods occurs under large-scale production conditions.

In some embodiments, the liquid culture medium used to cultivate the *Bordetella* species is a chemically defined liquid culture medium, such as Stainer-Scholte medium supplemented with dimethyl-β-cyclodextrin.

Further areas of applicability of the present disclosure will become apparent from the detailed description provided hereinafter. It should be understood that the detailed description and specific examples, while indicating some desirable aspects of the disclosure, are intended for purposes of illustration only and are not intended to limit the scope of the disclosure.

DETAILED DESCRIPTION

Figure 1:
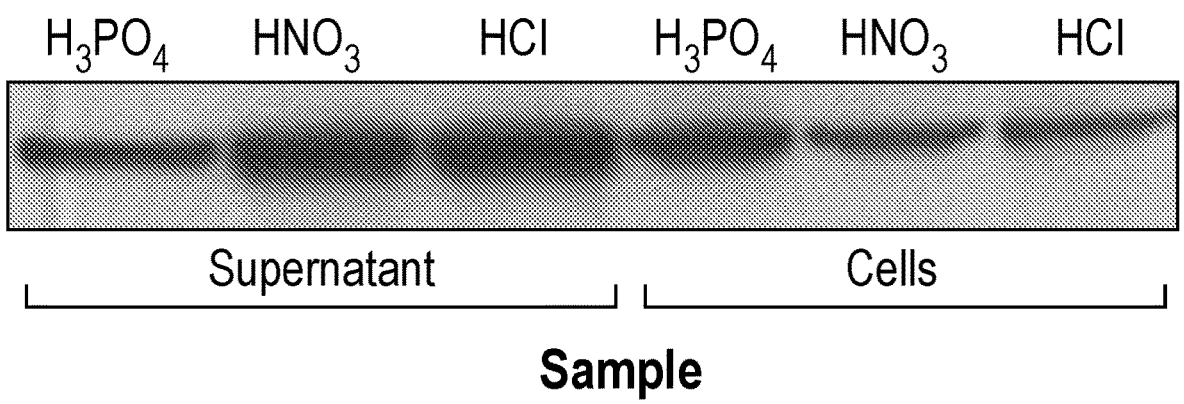
FIG. 1 depicts a Western blot showing the relative amounts of PRN in the supernatant or cellular fractions obtained from *Bordetella* cultures prepared using various acids to maintain pH control during *Bordetella* cultivation as described in Example 1.

The following description of various desirable aspect(s) is merely exemplary in nature and is in no way intended to limit the disclosure, its application, or uses.

As used in this specification and the appended claims, the singular forms "a," "an," and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

As used herein, "*Bordetella*" refers to a genus of small (0.2-0.7 µm), gram-negative coccobacilli of the phylum Proteobacteria. Typically, *Bordetella* species are obligate aerobes. Species of *Bordetella* are also highly fastidious, i.e., difficult to culture. All species can infect humans.

The term "cultivate" or "cultivating" as used herein refers to the growth of cells in a culture. The term "culture" as used herein refers to any growth of cells or organisms in a medium. The term "culture medium" or "medium" is recognized in the art, and refers generally to any substance or preparation used for the cultivation of living cells. The term "medium", as used in reference to a cell culture, includes the components of the environment surrounding the cells.

In various embodiments, the present method includes: cultivating a *Bordetella* species under aerobic conditions in a liquid culture medium; and maintaining a pH of the liquid culture medium during cultivation of said species, wherein maintaining the pH of the liquid culture medium comprises: adding an inorganic acid that dissociates essentially completely in water, such as nitric acid, to the liquid culture medium as needed to maintain the pH of the liquid culture medium within a predetermined range of pH values during cultivation of the *Bordetella* species.

Any liquid culture medium known in the art for cultivating *Bordetella* cells may be used with the present methods. In various embodiments, a complex medium is used. As used herein, a "complex medium" refers to a medium that contains peptone digests or extracts of plant or animal-origin. Examples of complex media suitable for use with the present methods include e.g., Hornibrook's medium, Cohen-Wheeler medium, B2 Medium, or other similar liquid culture media. A modified Stainer & Scholte medium that also includes dimethyl β cyclodextrin and casamino acids is another example suitable for use. Typically, however, a complex medium containing casamino acids is used initially during cultivation and later supplemented with a feeding supplement comprising growth factors and monosodium glutamate as the supply of nutrients is exhausted, as described in the Examples, below. As used herein, "casamino acids" refers to a mixture of amino acids obtained by the hydrolysis of casein.

In other embodiments, chemically defined medium is used with the instant methods to cultivate a *Bordetella* species. Chemically defined media are often considered to be beneficial since, unlike non-chemically defined media, chemically defined media contain a precise concentration of each nutrient, thus reducing variability of the medium and improving the quality of the fermented product. As used herein, the term "chemically defined medium" refers to a medium which is substantially devoid of complex material such as yeast, yeast extract, peptones, tryptones and casamino acids.

Table 1, below, provides examples of compositions of chemically defined media suitable for use with the instant method, i.e., Stainer & Scholte (SS) medium and (as modified version of SS medium (supplemented SS medium), which includes dimethyl-β-cyclodextrin, a growth stimulant of *B. pertussis*, and other minor changes. In these examples, the casamino acids in the complex medium have been replaced with selected amino acids. One or more additional amino acids may also be included.

TABLE 1

Composition of Stainer Scholte (SS) medium and supplemented SS medium

| Stainer Scholte | mg/L (SS) | mg/L (supplemented SS) |
|---|---|---|
| L-proline | 240 | 240 |
| Na-L-glutamate | 10,720 | 10,720 |
| L-cystine | 40 | 0 |
| NaCl | 2500 | 2500 |
| KH$_2$PO$_4$ | 500 | 500 |
| KCL | 200 | 200 |
| MgCl$_2$•6H$_2$0 | 100 | 100 |
| CaCl$_2$•2H$_2$0 | 20 | 20 |
| FeSO$_4$•7H$_2$0 | 10 | 10 |
| Tris | 6075 | 1820 |
| Ascorbic acid | 20 | 20 |
| Reduced glutathione (GSH) | 100 | 100 |
| Niacin (nicotinic acid) | 4 | 4 |
| dimethyl-β-cyclodextrin | 0 | 1000 |
| L-cysteine HCL | 0 | 40 |

In some embodiments, the liquid culture medium comprises a species of *Bordetella*. In various embodiments, the species of *Bordetella* is a species selected from the group consisting of *Bordetella avium, Bordetella hinzii, Bordetella trematum, Bordetella holmeshi, Bordetella parapertussis, Bordetella bronchiseptica* and *Bordetella perlussis* (otherwise known as *Haemophilus pertussis*). Typically, the species of *Bordetella* is selected from the group consisting of *Bordetella parapertussis, Bordetella bronchiseptica* and *Bordetella pertussis*. More typically, the species of *Bordetella* is *Bordetella pertussis*.

The fermentation process typically proceeds in at least two phases: (i) seed propagation and (ii) cultivation. The first phase is done in a shake flask. A relatively small seed culture is first grown by inoculation from a stock culture (e.g., working seed) and this is grown and used to inoculate a culture (e.g., seed culture, fermentation culture). More than one seed growth phase can be used to scale-up the quantity of *Bordetella* species for inoculation of the cultivation medium. Alternatively, growth of the species in the cultivation phase can proceed directly from the stored culture by direct inoculation, if desired. To start the cultivation phase, a portion or all of a seed culture is used to inoculate culture medium. There are one or more cultivation culture steps or passages. For example, to cultivate *Bordetella* in a 2000 L bioreactor, a seed culture can be used to inoculate a first culture vessel (20 L), that is used to inoculate a second culture vessel (200 L) and that is used to inoculate a third culture vessel (2000 L). By way of further example, to cultivate *Bordetella* in a 200 L vessel, a seed culture can be used to inoculate a primary flask that is used to inoculate a secondary flask, which is used to inoculate a 20 L vessel, which in turn is used to inoculate a 200 L vessel.

In some embodiments, cultivation of *Bordetella* species comprises growing *Bordetella* in a small vessel, such as a 2, 5 or 10 liter flask containing, for example, 1, 2, 3 or 5 liters of liquid culture medium. In other embodiments, the present method of cultivating *Bordetella* uses large-scale production conditions. As used herein, "large-scale production conditions" refer to cultivating cells in a culture vessel, typically a bioreactor, with a working volume of between 10 and 10,000 liters, between 25 and 5000 liters, between 25 and 2000 liters, between 50 liters and 1000 liters, between 100 liters and 5000 liters, between 500 liters and 8000 liters, between 1500 liters and 6500 liters, about 1500-1600 liters, about 3000-3200 liters, about 6000-6400 liters, greater than or equal to 25 liters, such as greater than or equal to 100 liters, such as at least 100 liters and less than or equal to 10,000 liters, such as at least 100 liters and less than or equal to 8000 liters, such as at least 100 liters and less than or equal to 4000 liters or such as at least 100 liters and less than or equal to 2000 liters.

In various embodiments, the cultivation process is carried out at a temperature of greater than or equal to 32° C., greater than or equal to 33° C., greater than or equal to 34° C., less than or equal to 45° C., less than or equal to 42° C., less than or equal to 40° C., less than or equal to 38° C., between 32° C. and 45° C., between 33° C. and 42° C., between 33° C. and 40° C. or between 33° C. and 38° C. Typically, cultivation is carried out a temperature ranging from 34° C. to 38° C.

Aeration may be achieved during cultivation by any method known in the art, such as by shaking or rolling the culture vessel or by the use of one or more impellers mounted on the shaft of a bioreactor. Alternatively, air or pure oxygen may be introduced into the culture vessel. The dissolved oxygen may be regulated to a level of e.g., about 20% to 40% or about 30% of air saturation. In some embodiments the level of dissolved oxygen is between 10 µM and 160 µM, between 15 µM and 140 µM, between 30 µM and 120 µM, between 45 µM and 15 µM, between 60 µM and 100 µM or around 80 µM.

In some embodiments, an antifoaming agent may be incorporated into the liquid culture medium during the cultivation process, such as polydimethylsiloxane.

In some embodiments, a cultivation period, ranges from 9 hours to 56 hours, such as 26 hours or less, or 48 hours or less. Each step of the cultivation process can have its own cultivation period.

Strong Acids

In various embodiments, the pH of the liquid culture medium is continuously assessed during cultivation of the organism and an acid is fed to the liquid culture medium, as required, in a concentration sufficient to maintain the pH of the culture medium within a predetermined range of values during growth of the organism. Generally, the range of pH within which the culture medium is controlled throughout the cultivation typically is from about 6.0 to about 9.0, more typically from about 6.8 to about 7.3, such as from about 7.0 to 7.2. The determination of pH and, as necessary, adjustment, typically is effected automatically, for example, using a pH meter operatively connected to a pump, which may be a peristaltic pump, for pumping acid to the liquid culture medium in response to pH determinations outside a predetermined range.

As used herein, an "acid" refers to a substance that, when added to an aqueous solution, donates protons to water molecules ($H_2O$). Typically, a strong acid, such as a strong inorganic acid, is used to maintain the pH of the culture medium. As used herein, "a strong acid" is one that dissociates essentially completely in water. In contrast, a mild or weak acid is an acid that dissociates incompletely in water. That is, a mild or weak acid does not release all of its hydrogens in a solution, donating only a partial amount of its protons to the solution.

Strong acids may also be defined in reference to Ka and/or pKa values. As used herein, Ka refers to an equilibrium constant in a dissociation equilibrium state: $[H^+][A^-]/[HA]$. That is, the numerical value of Ka is equal to the concentration of the products divided by the concentration of the reactants, where the reactant is the acid (HA) and the products are the conjugate base and H. As used herein, pKa means an acid dissociation constant that is a constant defined by $pKa = -\log_{10}Ka$.

For example, water ($H_2O$) is the base of the hydronium ion, $H_3O^+$, which has a pKa of 0 at 25° C. An acid having a pKa less than that of hydronium ion is considered a strong acid. Hydrochloric acid (HCl), for example, has a pKa of −7, which is less than the pKa of the hydronium ion. This means that HCl will give up its protons to water, essentially completely, to form the $H_3O^+$ cation. For this reason, HCl is classified as a strong acid in water. One can assume that all of the HCl in a water solution is 100% dissociated, meaning that both the hydronium ion concentration and the chloride ion concentration correspond directly to the amount of added HCl.

Examples of other strong acids in addition to HCl that may be used to control the pH in the instant *Bordetella* cultivation methods include hydrobromic, sulfuric, nitric, chloric, perchloric, permanganic, and hydroiodic acids. However, hydrochloric acid (HCl), sulfuric acid ($H_2SO_4$) or nitric acid ($HNO_3$) are typically used. Even more typically, the strong acid used with the instant methods is nitric acid ($HNO_3$).

In contrast to the strong acids disclosed herein, "a mild or weak acid" refers to those acids having a Ka value of less than about $10^{-1}$ or a pKa value greater than 1. Examples of mild or weak acids include phosphoric, phosphorous, nitrous and sulfurous acids. Other examples of strong and weak acids and their Ka and pKa values are shown below in Table 2.

TABLE 2

Ka and pKa of strong and weak acids suitable for use with the instant methods

| Acid | HA | A− | Ka | pKa | Acid Strength |
|---|---|---|---|---|---|
| Hydroiodic | HI | I− | Strong acids completely dissociate in aqueous solution (Ka > 1, pKa < 1). | | |
| Hydrobromic | HBr | $Br^-$ | | | |
| Perchloric | $HClO_4$ | $ClO_4^-$ | | | |
| Hydrochloric | HCl | $Cl^-$ | | | |
| Chloric | $HClO_3$ | $ClO_3^-$ | | | |
| Sulfuric (1) | $H_2SO_4$ | $HSO^-$ | | | |
| Nitric | $HNO_3$ | $NO_3^-$ | | | |
| Hydronium ion | $H_3O+$ | $H_2O$ | 1 | 0.0 | ↑ |
| Iodic | $HIO_3$ | $IO_3^-$ | $1.6 \times 10^{-1}$ | 0.80 | |
| Oxalic (1) | $H_2C_2O_4$ | $HC_2O_4^-$ | $5.9 \times 10^{-2}$ | 1.23 | |
| Sulfurous (1) | $H_2SO_3$ | $HSO_3^-$ | $1.54 \times 10^{-2}$ | 1.81 | |
| Sulfuric (2) | $H_2SO_4$ | $SO_4^{2-}$ | $1.2 \times 10^{-2}$ | 1.92 | |
| Chlorous | $HClO_2$ | $C1O_2^-$ | $1.1 \times 10^{-2}$ | 1.96 | |
| Phosphoric (1) | | $H_2PO_4^-$ | $7.52 \times 10^{-3}$ | 2.12 | |
| Arsenic (1) | $H_3AsO_4$ | $H_2AsO_4^-$ | $5.0 \times 10^{-3}$ | 2.30 | |
| Chloroacetic | $CH_2ClCOO$ | $CH_2ClCOO^-$ | $1.4 \times 10^{-3}$ | 2.85 | |
| Hydrofluoric | HF | $F^-$ | $7.2 \times 10^{-4}$ | 3.14 | |
| Nitrous | $HNO_2$ | $NO_2^-$ | $4.0 \times 10^{-4}$ | 3.39 | |
| Formic | HCOOH | $HCOO^-$ | $1.77 \times 10^{-4}$ | 3.75 | |
| Lactic | $HCH_3H_5O_3$ | $CH_3H_5O_3^-$ | $1.38 \times 10^{-4}$ | 3.86 | |
| Ascorbic (1) | $H_2C_6H_6O_6$ | $HC_6H_6O_6^-$ | $7.9 \times 10^{-5}$ | 4.10 | |
| Benzoic | $C_6H_5COOH$ | $C_6H_5COO^-$ | $6.46 \times 10^{-5}$ | 4.19 | |
| Oxalic (2) | $HC_2O_4$ | $C_2O_4^{2-}$ | $6.4 \times 10^{-5}$ | 4.19 | |
| Hydrazoic | $HN_3$ | $N_3^-$ | $1.9 \times 10^{-5}$ | 4.72 | |
| Citric (2) | $H_2C_6H_5O_{7-}$ | $HC_6H_5O_7^{2-}$ | $1.8 \times 10^{-5}$ | 4.74 | |
| Acetic | $CH_3COOH$ | $CH_3COO^-$ | $1.76 \times 10^{-5}$ | 4.75 | |
| Propionic | $CH_3CH_2CO$ | $CH_3CH_2COO^-$ | $1.34 \times 10^{-5}$ | 4.87 | |
| Pyridinium ion | $C_5H_4NH+$ | $C_5H_4N$ | $5.6 \times 10^{-6}$ | 5.25 | |
| Carbonic (1) | $H_2CO_3$ | $HCO_3^-$ | 4.3 × 10−7 | 6.37 | |
| Sulfurous (2) | $HSO_4$ | $SO_4^{2-}$ | $1.02 \times 10^{-7}$ | 6.91 | |
| Phosphoric (2) | $H_2PO_{4-}$ | $HPO_4^{2-}$ | $6.23 \times 10^{-8}$ | 7.21 | |
| Hypochlorous | HClO | $ClO^-$ | $3.5/3.0 \times 10^{-8}$ | 7.46/7.53 | |
| Hypobromous | HBrO | BrO− | $2 \times 10^{-9}$ | 8.70 | |
| Ascorbic (2) | $HC_6H_6O_6^-$ | $C_6H_6O_6^{2-}$ | $1.6 \times 10^{-12}$ | 11.80 | |
| Phosphoric (3) | $HPO_4^{2-}$ | $PO_4^{3-}$ | $4.8/202 \times 10^{-13}$ | 12.32/12.66 | |

In some embodiments, a solution comprising only one acid, such as only one strong acid, such as only one strong inorganic acid, e.g., nitric acid, is used to maintain the pH of the liquid culture medium of the instant methods. That is, 100% of the acid in the solution used to control the pH is a strong acid, such as a strong inorganic acid, such as HCl, $H_2SO_4$ or $HNO_3$. In some embodiments, the molarity of the solution comprising only the one acid, such as only one strong acid, such as only one strong inorganic acid, e.g., nitric acid, ranges from 0.5 M to 5.0 M, such as 1.0 M to 4.0 M, such as about 3.5 M, such as 3.5 M nitric acid or 3.5 M HCl. Typically, 3.5 M nitric acid is used with the instant methods.

In various embodiments, cultivation is typically followed by a step to separate the culture medium into a cellular fraction and a supernatant fraction, using, for example, centrifugation. One or more antigens from the *Bordetella* culture, including PRN, PT, FHA and FIM2/3 can be further isolated from the cellular and supernatant fractions using methods available in the art, including those described in U.S. Pat. No. 5,877,298, which is hereby incorporated by reference in its entirety. The term "antigen" or "immunogen", as used herein, refers to a molecule that contains one or more epitopes (linear, conformational or both) that upon exposure to a subject, e.g., a mammal such as a human, will induce an immune response that is specific for that antigen. An epitope is the specific site of the antigen which binds to a T-cell receptor or specific antibody, and typically comprises about 3 amino acid residues to about 20 amino acid residues. The term antigen refers to subunit antigens: antigens that are separate and discrete from a whole organism with which the antigen is associated in nature.

The term "isolated" or "isolating" refers to a substance that is either in substantially pure form, for example, greater than about 95% purity or which is at least partially purified, for example, greater than 85% pure, greater than 75% pure or greater than 50% pure or which is removed in some way from its natural environment or its growth medium. Accordingly, any reference to "isolated" or "isolating" encompasses an agent, such as an antigen, that is removed from its liquid culture medium and/or from a whole cell bacterial preparation, and which may be substantially or at least partially purified, including, for example, cellular or supernatant fractions obtained by centrifugation of the *Bordetella* culture medium. The term "isolated" also encompasses immunogens that are in solution with other agents, diluents, excipients, adjuvants and/or proteins.

Isolating antigens, such as PRN, may be carried out by any method known in the art, e.g., such as described in U.S. Pat. Nos. 5,667,787 and 5,877,298, which are herein incorporated by reference in its entirety Typically, the isolation process begins by separating the liquid culture medium into an aqueous material also referred to herein as a supernatant fraction or centrate and a cellular fraction. Separation can be achieved by various methods. For instance, solids in the culture can be allowed to settle under gravity and the aqueous material can then be removed by decanting or by aspiration. Typically, however, centrifugation is used to give a solid pellet and a supernatant, which can easily be separated. The pellet includes *Bordetella* cells and other insoluble materials. The supernatant includes culture medium and any components released by the bacteria during culture.

The supernatant, which typically contains PT, FHA and PRN, may be filtered and then concentrated by using, e.g., cellulose membranes. PT, FHA and PRN may be separated by perlite fractionation, for example. The PRN may be collected in the run through of the column used in this separation step, while PT and FHA may be eluted off the column, if desired.

In some embodiments, PRN is precipitated in three consecutive precipitation steps using ammonium sulphate at three different concentrations as described, for example, in U.S. Pat. No. 5,667,787, which is herein incorporated by reference in its entirety. For example, in the first and third precipitation, the pellet is the fraction of interest while in the second precipitation the supernatant is used. The final pellet collected by centrifugation may then be dissolved in, e.g., 10 mM HCl Tris buffer and loaded onto a chromatography column. The product may then be ultrafiltered and diafiltered before being subjected to a final chromatography step. The final filtration may involve a pre-filtration step and a sterile filtration (0.2 μm filter) prior to quantification of the PRN.

In some embodiments, the purified PRN is adsorbed onto an adjuvant, such as aluminum phosphate. As is known in the art, adjuvants are compounds that serve to enhance the immune system in response to an antigen. In the adsorption process, an aluminum phosphate solution, for example, is added to the antigen, and mixed for 4 days at 16° C. to 24° C. After the adsorption, the PRN may be stored at 2° C. to 8° C. for up to 36 months.

In some embodiments, when a solution comprising only one acid, such as only one strong acid, such as only one strong inorganic acid, e.g., nitric acid or hydrochloric acid, such as a solution comprising 100% 3.5 M nitric acid or 100% 3.5 M hydrochloric acid is used to maintain the pH during *Bordetella* cultivation according to the instant methods, PRN is increased in the supernatant in comparison to an amount of PRN in the supernatant when the pH is maintained using only one or more weaker or milder acids as defined herein, such as phosphoric acid ($H_3PO_4$), e.g., a solution comprising 100% 2.5 M phosphoric acid.

In some embodiments, when a solution comprising only one acid, such as only one strong acid, such as only one strong inorganic acid, e.g., nitric acid or hydrochloric acid, such as a solution comprising 100% 3.5 M nitric acid or 100% 3.5 M hydrochloric acid is used to maintain the pH during *Bordetella* cultivation according to the instant methods, PRN is increased in the supernatant by about 1×, 2×, 3×, 4×, 5×, 6× or 10×, typically about 3×-6× in comparison to an amount of PRN in the supernatant when the pH is maintained using only one or more weaker or milder acids as defined herein, such as phosphoric acid ($H_3PO_4$), e.g., a solution comprising 100% 2.5 M phosphoric acid.

In some embodiments, when a solution comprising only one acid, such as only one strong acid, such as only one strong inorganic acid, e.g., nitric acid or hydrochloric acid, such as a solution comprising 100% 3.5 M nitric acid or 100% 3.5 M hydrochloric acid is used to maintain the pH during *Bordetella* cultivation according to the instant methods, PRN is correspondingly decreased by about 10%, 25%, 50%, 75% or 100%, typically 50% in the cellular fraction in comparison to an amount of PRN in the cellular fraction when the pH is maintained using only one or more weaker or milder acids as defined herein, such as phosphoric acid ($H_3PO_4$), e.g., a solution comprising 100% 2.5 M phosphoric acid.

The present disclosure is also directed to a method for increasing a yield of fimbrial agglutinogen 2 and fimbrial agglutinogen 3 in a supernatant fraction from a *Bordetella* culture, which method comprises: cultivating a *Bordetella* species under aerobic conditions in a liquid culture medium as described herein; maintaining a pH of the liquid culture medium during cultivation of said species, wherein maintaining the pH of the liquid culture medium comprises: adding an acid to the culture medium as needed to maintain the pH of the culture medium within a predetermined range of pH values during cultivation of said *Bordetella* species as described herein, wherein the acid comprises an inorganic acid that dissociates essentially completely in water, i.e., as strong acid, as described herein and separating the liquid culture medium after cultivation of *Bordetella* into a cellular fraction and a supernatant fraction (centrate); and isolating Fimbriae Types 2 and 3 from the cellular faction and/or supernatant fraction.

In some embodiments, FIM2/3 is isolated from the *Bordetella* culture. In these embodiments, the liquid culture medium used for cultivation may be a complex medium or a chemically defined medium. Typically, in these embodiments, the liquid culture medium is a chemically defined medium as described herein, e.g., supplemented SS medium. In various embodiments, FIM2/3 is obtained from the supernatant and/or cellular fraction after separating the liquid culture medium into a cellular fraction and a supernatant fraction as described herein, e.g., by centrifugation. FIM2/3 can be isolated from the supernatant fraction and/or cellular fraction according to any method known in the art. In certain embodiments, FIM2/3 is isolated from the supernatant fraction. In other embodiments, FIM2/3 is isolated from the cellular fraction. For example, FIM2/3 can be isolated from the cellular fraction by lysing the cells using techniques known in the art (e.g., urea, heat or sonication) followed by further isolation of FIM2/3.

In some embodiments, when a solution comprising only one acid, such as only one strong acid, such as only one strong inorganic acid, e.g., nitric acid, sulfuric acid, or hydrochloric acid, such as a solution comprising 100% 3.5 M nitric acid or 100% 3.5 M hydrochloric acid is used to maintain the pH during *Bordetella* cultivation according to the instant methods, FIM2/3 is increased in the supernatant in comparison to an amount of FIM2/3 in the supernatant when the pH is maintained using only one or more weaker or milder acids as defined herein, such as phosphoric acid ($H_3PO_4$), e.g., a solution comprising 100% 2.5 M phosphoric acid.

In some embodiments, when a solution comprising only one acid, such as only one strong acid, such as only one strong inorganic acid, e.g., nitric acid, sulfuric acid or hydrochloric acid, such as a solution comprising 100% 3.5 M nitric acid or 100% 3.5 M hydrochloric acid is used to maintain the pH during *Bordetella* cultivation according to the instant methods, FIM2/3 is increased in the supernatant by about 1×, 2×, 3×, 4×, 5×, 6× or 10×, typically about 3× in comparison to an amount of FIM2/3 in the supernatant when the pH is maintained using only one or more weaker or milder acids as defined herein, such as phosphoric acid ($H_3PO_4$), e.g., a solution comprising 100% 2.5 M phosphoric acid.

Acid Blends

The present disclosure is also directed to a method for cultivating a species of *Bordetella*, as described herein, which method comprises: cultivating a *Bordetella* species under aerobic conditions as described herein in a liquid culture medium; and maintaining a pH of the liquid culture medium during cultivation of said species, wherein maintaining the pH of the liquid culture medium comprises: adding a first and second acid to the culture medium as needed to maintain the pH of the liquid culture medium within a predetermined range of pH values as described herein during cultivation of said *Bordetella* species, wherein said first acid is an inorganic acid that dissociates essentially completely in water, and wherein said second acid is an inorganic or organic acid having an acid dissociation constant (pKa) of greater than 1.

In various embodiments, the pH of the liquid culture medium is maintained during *Bordetella* cultivation by using a blend of a first and a second acid. In some embodiments that use acid blends to control pH, the liquid culture medium may be a complex medium or a chemically defined medium. Typically, however, the liquid culture medium is a chemically defined medium as described herein, e.g., supplemented SS medium.

In some embodiments that use acid blends for pH control, the first acid is a strong acid, i.e. an acid that dissociates essentially completely in water, as described herein. More typically, the first acid is a strong inorganic acid such as hydrobromic, sulfuric, nitric, chloric, perchloric, permanganic, and hydroiodic acids. However, even more typically, the first acid is hydrochloric acid (HCl), sulfuric acid ($H_2SO_4$) or nitric acid ($HNO_3$). Yet even more typically, the strong acid is nitric acid ($HNO_3$).

In various embodiments, a second acid is also used to maintain the pH of the culture medium. Typically, the second acid is a weaker acid than the first acid. The first acid is mixed with the second acid resulting in a conjugate acid-base pair in which the second acid, being a weaker acid, effectively functions as a base to accept hydrogen ions ($H^+$) from the first acid. In various embodiments, this second acid is selected from the group of acids having a Ka value of less than about $10^{-1}$ or a pKa value greater than 1. Examples of weaker acids for use with the present methods are shown in Table 2. Typically, the weaker acids include inorganic acids such as chlorous, hydrazoic, hydrofluoric, hydrosulfuric, hydrosulfurous, hypobromous, hypochlorous, hypophosphorous, iodic, nitrous, phosphoric, phosphorous, pyrophosphoric, and sulfurous acids. More typically, the weaker acid is phosphoric acid ($H_3PO_4$).

In some embodiments, the weaker acid is an organic acid. Organic acids tend to dissociate more slowly than inorganic acids and less completely. Examples of organic acids having a Ka value of less than about $10^{-1}$ or a pKa value greater than 1 that may be combined with a first acid, i.e., a strong acid, for use with the present methods are also shown in Table 2. Suitable organic acids include, e.g., acetic acid, lactic acid and ascorbic acid. For example, acetic acid ($CH_3CO_2H$) has a pKa of 4.75, greater than that of the hydronium ion, but less than that of water itself, i.e. 14 (at 25° C.). This means that acetic acid can dissociate in water, but only to a small extent. Thus, acetic acid is classified as a weak acid and can be combined with a strong acid of the instant disclosure to maintain the pH of the liquid culture medium during *Bordetella* cultivation.

In some embodiments, the blended acid solution comprises up to about 99%, such as about 98%, such as about 97%, such as about 95%, such as about 90%, such as about 80%, such as about 75%, such as about 70%, such as about 60%, such as about 55%, such as about 50%, such as about 45%, such as about 40%, such as about 35%, such as about 30%, such as about 25%, such as about 20%, such as about 10%, such as about 5%, such as about 1% of a strong acid, wherein the remainder of the blended acid solution comprises a weaker acid (v/v) i.e., an acid having a pKa greater than 1.

In some embodiments, the blended acid solution comprises up to about 99%, such as about 98%, such as about 97%, such as about 95%, such as about 90%, such as about 80%, such as about 75%, such as about 70%, such as about 60%, such as about 55%, such as about 50%, such as about 45%, such as about 40%, such as about 35%, such as about 30%, such as about 25%, such as about 20%, such as about 10%, such as about 5%, such as about 1%, of a weak acid having a pKa greater than 1, wherein the remainder of the blended acid solution comprises the strong acid (v/v), i.e., an acid that dissociates essentially completely in water.

Typically, the blended acid solution comprises between 30% and 50%, such as about 40% of the strong acid as defined herein, such as a strong inorganic acid, such as nitric acid, sulfuric acid or hydrochloric acid and between 50% and 70%, such as about 60% of a weaker acid having a pKa value greater than 1 (v/v). Typically, the second acid having a pKa greater than 1 is phosphoric acid.

In some embodiments, the molarity of a solution comprising a strong acid as defined herein, which is used in the instant blended acid solution, such as a strong inorganic acid, e.g., nitric acid, ranges from 0.5 M-5.0 M, such as 1.0 M-4.0 M, such as 3.5 M, such as 3.5 M nitric acid or 3.5 M HCl, typically 3.5 M nitric acid.

In some embodiments, the molarity of a solution comprising a weak acid as defined herein, which is used in the blended acid solution, such as a weak organic or inorganic acid, e.g., phosphoric acid, ranges from 0.5 M-5.0 M, such as 1.0 M-4.0 M, such as 3.5 M, such as 2.5 M, such as 2.5 M phosphoric acid. In some embodiments, the blended acid solution comprises between 30% and 50% of 3.5 M HCl or 3.5 M $HNO_3$ and between 50% and 70% of 2.5 M $H_3PO_4$. Typically, the blended acid solution comprises about 40% 3.5 M HCl or 3.5 M $HNO_3$ and about 60% 2.5 M $H_3PO_4$. Even more typically, the blended acid solution comprises about 40% 3.5 M $HNO_3$ and about 60% 2.5 M $H_3PO_4$.

In some embodiments, when a solution comprising the first and second acids as described herein is used to maintain the pH during *Bordetella* cultivation according to the instant methods, such as a solution comprising about 40% 3.5 M nitric acid and about 60% 2.5 M phosphoric acid, PRN is increased in the supernatant by about 1×, 2×, 3×, 4×, 5×, 6× or 10×, typically about 2×-3× in comparison to an amount of PRN in the supernatant when the pH is maintained using only one or more weaker or milder acids as defined herein, such as phosphoric acid ($H_3PO_4$), e.g., a solution comprising 100% 2.5 M phosphoric acid.

In some embodiments, the increase in PRN observed in the supernatant is not accompanied by a decrease in the amount of other antigens in the supernatant. For example, in some embodiments, when a solution comprising the first and second acids as described herein is used to maintain the pH during *Bordetella* cultivation according to the instant methods, such as a solution comprising about 40% 3.5 M nitric acid and about 60% 2.5 M phosphoric acid, PRN is increased in the supernatant without a concomitant or substantial decrease of PT or FHA in the supernatant in comparison to an amount of PT or FHA in the supernatant when the pH is maintained using only one or more weaker or milder acids as defined herein, such as phosphoric acid ($H_3PO_4$), e.g., a solution comprising 100% 2.5 M phosphoric acid.

In some embodiments, the increase in PRN observed in the supernatant is not accompanied by a decrease in the amount of other antigens in the cellular fraction. For example, in some embodiments, when a solution comprising the first and second acids as described herein is used to maintain the pH during *Bordetella* cultivation according to the instant methods, such as a solution comprising about 40% 3.5 M nitric acid and about 60% 2.5 M phosphoric acid, PRN is increased in the supernatant without a concomitant or substantial decrease of FIM2/3 in the cellular fraction in comparison to an amount of FIM2/3 in the cellular fraction when the pH is maintained using only one or more weaker or milder acids as defined herein, such as phosphoric acid ($H_3PO_4$), e.g., a solution comprising 100% 2.5 M phosphoric acid.

As used herein, "without a substantial decrease" in reference to an amount of *Bordetella* antigen means a decrease of about 25% or less, such as 20% or less, such as 15% or less, such as 10% or less, such as 5% or less or such as 2% or less in comparison to the amount of *Bordetella* antigen observed or isolated from a *Bordetella* culture when a blended acid solution as described herein is not used to maintain the pH of the *Bordetella* culture from which the supernatant and cellular fraction are obtained, such as when a solution of 2.5 M phosphoric acid or a solution of another weak acid as described herein is used to maintain the pH of the *Bordetella* liquid culture medium during cultivation.

Any method known in the art may be used to obtain the antigens PRN, PT, FHA and FIM2/3 after cultivating the *Bordetella* species according to the instant methods wherein the first and second acids are used for pH control as described herein. As noted previously, PRN can be isolated according to art-known methods.

PT can be isolated, for example, as described in Example 2 of U.S. Pat. No. 5,877,298, which is incorporated by reference herein in its entirety. PT can also be isolated, for example, using the methods described in U.S. Pat. No. 5,085,862, WO96/34623, U.S. Pat. No. 4,705,868, EP0336736, WO9115505, EP0306318, EP0322533, EP0396964, EP0275689, WO91/12020, EP0427462, WO9819702 and U.S. Pat. No. 4,784,589, each of which is incorporated by reference herein in its entirety.

FHA can, for instance, be isolated as described in Example 2 of U.S. Pat. No. 5,877,298, which is incorporated herein by reference in its entirety. FHA can also, for instance, be isolated as described in WO9013313, EP0484621, WO9634623, EP0336736, WO9115505, U.S. Pat. No. 4,784,589, and WO9004641, each of which is incorporated by reference herein in its entirety.

FIM2/3 can be isolated from the cellular fraction as described, for example, in U.S. Pat. No. 5,877,298, which is incorporated herein by reference in its entirety FIM2/3 can also, for instance, be isolated as described in U.S. Pat. Nos. 4,784,589, 6,475,754, EP0555894, WO9858668, and WO0207764, each of which is incorporated by reference herein in its entirety.

In some embodiments, FIM2/3 is isolated from the supernatant, rather than the cellular fraction. Typically, in these embodiments, the instant cultivation methods comprise a chemically defined, rather than a complex liquid culture medium.

In some embodiments, when a solution comprising the first and second acids as described herein is used to maintain the pH during *Bordetella* cultivation according to the instant methods, such as a solution comprising about 40% 3.5 M nitric acid and about 60% 2.5 M phosphoric acid, FIM2/3 is increased in the supernatant by about 1×, 2×, 3×, 4×, 5×, 6× or 10×, typically about 3× in comparison to an amount of FIM2/3 in the supernatant when the pH is maintained using only one or more weaker or milder acids as defined herein, such as phosphoric acid ($H_3PO_4$), e.g., a solution comprising 100% 2.5 M phosphoric acid.

Formulating Vaccines

In some embodiments, one or more of the isolated antigens as described herein are formulated into an immunogenic composition or subunit vaccine. A "subunit vaccine", as used herein, refers to a type of vaccine that includes one or more antigens—but not all antigens—which are derived from or homologous to, antigens from a pathogen of interest, such as a virus, bacterium, parasite, fungus, or fungal-like organism. Such a vaccine is substantially free of intact pathogen cells or pathogenic particles, or the lysate of such cells or particles. Thus, a subunit vaccine or subunit composition can be prepared from at least partially purified, or substantially purified, immunogenic polypeptides from the pathogen or their analogs. Methods of obtaining an antigen or antigens in the subunit vaccine include standard purification techniques, recombinant production, or chemical synthesis. A "subunit vaccine" thus refers to a vaccine consisting of a defined antigenic component or components of a virus, bacterium, or other immunogen.

In various embodiments, the one or more antigens are formulated into a human dose of a subunit vaccine. A "human dose" as used herein refers to an amount of vaccine that is administered to a human in a single administration. Typically, this amount is present in a volume of 0.1-2 milliliters, e.g., 0.2-1 milliliters, typically 0.5 milliliters. The indicated amounts may, thus, for instance, be present at a concentration of micrograms per 0.5 milliliters bulk vaccine. In certain embodiments a (single) human dose thus equals 0.5 milliliters.

In some embodiments, the one or more antigens that are formulated into a vaccine comprise PT and FHA. In some embodiments, the one or more antigens that are formulated into a vaccine comprise PT, FHA, and FIM2/3, and PRN.

In some embodiments, incorporation of PT into a vaccine comprises detoxification of PT. PT can be chemically or genetically detoxified. Chemical detoxification can, for instance, be performed by any of a variety of conventional chemical detoxification methods, such as treatment with formaldehyde, hydrogen peroxide, tetranitromethane, or glutaraldehyde. For instance, detoxification can be performed as described in example 3 of U.S. Pat. No. 5,877,298, which is herein incorporated by reference in its entirety.

In certain embodiments, PT is genetically detoxified. This can be accomplished by mutating pertussis toxin gene to inactivate the enzymatic activity of the catalytic subunit S1 of pertussis toxin, as has been described, for example, in U.S. Pat. Nos. 7,144,576, 7,666,436, and 7,427,404, and which are each herein incorporated by reference in its entirety.

In certain embodiments, formulating the present antigens into a vaccine comprises incorporating an amount of PT ranging from 2-50 µg, 5-40 µg, 10-30 µg, or 20-25 µg per human dose.

In certain embodiments, formulating the present antigens into a vaccine comprises incorporating an amount of FHA ranging from 2-50 µg, 5-40 µg, 10-30 µg, or 20-25 µg per human dose.

In certain embodiments, formulating the present antigens into a vaccine comprises incorporating an amount of PRN ranging from 0.5-100 µg, 1-50 µg, 2-20 µg, 3-30 µg, 5-20 µg, or 6-10 µg per human dose.

In certain embodiments, the weight ratio of FIM 2 to FIM 3, which may be formulated into a vaccine is from about 1:3 to about 3:1, e.g., from about 1:1 to about 3:1, e.g., from about 1.5:1 to about 2:1. In certain embodiments, formulating the present antigens into a vaccine comprises incorporating an amount of FIM2/3 ranging from 1-100 µg per human dose, such as 3-50 µg, or 3-30 µg, such as 5 µg per human dose.

In certain embodiments, the antigens that are formulated into immunogenic compositions or vaccines may be further formulated with antigens from one or more pathogens other than from *Bordetella*. For example, in certain embodiments, the formulations comprise one or more of the following: tetanus toxoid (TT), diphtheria toxoid (DT), *Haemophilus influenzae* type-b oligosaccharide or polysaccharide conjugate (Hib), hepatitis B virus surface antigen (HBsAg) and/or inactivated polio virus (IPV).

The present antigens, which are formulated as immunogenic compositions or vaccines may be formulated as injectibles, as liquid solutions or emulsions. For example, the present *Bordetella* antigens may be mixed with pharmaceutically acceptable excipients which are compatible with the antigens. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof.

Immunogenicity may be significantly improved if the antigens are co-administered with adjuvants, commonly used as 0.005 to 0.5 percent solution in phosphate buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Typically, aluminum hydroxide and aluminum phosphate (collectively commonly referred to as alum) may be used to formulate vaccines prepared from the instant *Bordetella* cultivation methods.

EXAMPLES

Example 1. Strong Acids Increase PRN Yield in Supernatant from *Bordetella* Culture A working seed (2.5 mL) was inoculated in 2 L shake flasks each containing 500 mL of broth (modified Stainer-Scholte medium, Table 3) with 5 mL of 100× growth factor solution (Table 4). Cultures were grown for 44 hours in an incubator shaker and used to inoculate 2 L fermenters/bioreactors (2 L BIOSTAT B fermenters (B. Braun Biotech International, Berlin, Germany) containing 1150 mL of broth (modified Stainer-Scholte medium, Table 3) supplemented with growth factor solution (Table 4).

During the period of cultivation, a feeding supplement of monosodium glutamate and the growth factors, glutathione, ferrous sulphate, ascorbic acid, nicotinic acid and cysteine were continuously added to the bioreactor to increase antigen yields. The addition of supplement solution was triggered by a sharp increase in the dissolved oxygen (DO) level and a sharp decrease in agitation, which occurs after consumption of the initial carbon sources during the batch cultivation phase. The bioreactors each worked under the same operating conditions in terms of temperature (36° C.±2° C.), dissolved oxygen (35%), agitation (100-675 rpm) and pH (7.2) levels and were continuously monitored and controlled. 2.5 M phosphoric acid, 3.5 M nitric acid or 3.5 M hydrochloric acid was used to maintain the pH in each bioreactor. Antifoam was added continuously for foam control. Cultivation time was about 48 hours.

At the end of the cultivation period, the broth was centrifuged to obtain a cellular fraction and a supernatant fraction. Each fraction was assayed for PRN by ELISAs and Western blotting. Supernatant samples for PRN, PT and FHA ELISA analysis were prepared by diluting samples by dilution factors between 1/100 and 1/200 for PRN, between 1/20 and 1/40 for FHA and between 1/40 for PT. Cell pellet lysate samples for PRN ELISA were prepared by resuspending the cell pellet in a lysis buffer with Triton X-100 added to a final concentration of 0.5% and 0.25 mg/mL lysozyme. Sample lysate was diluted 1/100 for ELISA assays.

TABLE 3

Modified Stainer-Scholte medium

| SS | Mg/L |
| --- | --- |
| NaCl | 2,500 |
| $KH_2PO_4$ | 500 |
| KCl | 200 |
| $MgCl_2 \cdot 6H_2O$ | 100 |
| Tris base | 1,500 |
| Casamino acid | 10,000 |
| Monosodium glutamate | 10,000 |

TABLE 4

Growth Factors

| SS Complex Medium Growth Factors (100 X) | Mg/L |
| --- | --- |
| L-cysteine HCl | 40 |
| Nicotinic acid | 4 |
| Ascorbic acid | 400 |
| Glutathione, reduced | 150 |
| $FeSO_4 \cdot 7H_2O$) | 10 |
| Heptakis-(2-6-0-dimethyl)-β-cyclodextrin | 1000 |
| $CaCl_2 \cdot 2H_2O$ | 20 |

Relative quantities of PRN in the supernatant fraction are shown in Table 5 (below) and FIG. 1. When 2.5 M phosphoric acid was replaced with another solution for pH control, such as 3.5 M nitric acid or 3.5 M hydrochloric acid, the PRN yield in the supernatant of the bioreactor harvest was increased to 15-30 mg/L from about 4-5 mg/L. An examination of the relative amount of PRN associated with the cellular fraction and present in the supernatant by Western Blotting of samples from the bioreactor harvest indicated that the overall expression of PRN *B. pertussis* may not have increased substantially in response to the use of acid alternatives to phosphoric acid for bioreactor pH control, but, instead, the increase in the PRN in the supernatant corresponded to a decrease in the amount that was associated with the harvested cells (i.e. more released from the cells into the supernatant).

TABLE 5

ELISA detection of PRN in supernatant fraction.

| Acid used for bioreactor pH control | 2.5M phosphoric acid | 3.5M nitric acid | 3.5M hydrochloric acid |
| --- | --- | --- | --- |
| PRN yield in supernatant (mg/L) | 4.9-5.3 (2 runs) | 14.6-21.8 (2 runs) | 30.7 (1 run) |

Table 6 shows that the yields of other antigens in the supernatant, however, did not increase with the use of acids alternative to 2.5 M phosphoric acid. For example, Table 6 depicts the lower yields of PT (about 19 to 24.5 mg/L) and FHA (about 120 to 124 mg/L) as measured by ELISA after cultivation using 3.5 M nitric acid or 3.5 M hydrochloric acid, respectively, for bioreactor pH control in comparison to the yield when 2.5 M phosphoric acid was used (33.2 mg/L, PT; 194.1 mg/L, FHA).

TABLE 6

ELISA detection of PT and FHA in supernatant samples from a bioreactor harvest.

| Acid used for bioreactor pH control | 2.5M phosphoric acid | 3.5M nitric acid | 3.5M hydrochloric acid |
| --- | --- | --- | --- |
| PT yield in the supernatant (mg/L) | 33.2 | 18.8 | 24.5 |
| FHA yield in supernatant (mg/L) | 194.1 | 119.8 | 124.2 |

Example 2. Acid Blends Increase PRN and FIM2/3 Yield in Supernatant from *Bordetella* Culture while Mitigating PT and FHA Loss Cultures were prepared as described above for Example 1, except that blends of nitric acid and phosphoric acid at different ratios were used for bioreactor pH control. PRN, PT, FHA and FIM2/3 antigens were isolated to assess the effect of the acid blends on antigen production. At the end of the cultivation period, the harvest was centrifuged to obtain a cellular fraction and a supernatant fraction. The supernatant fraction was assayed for PRN, PT, FHA and FIM2/3 antigens by ELISA. The cell pellet was resuspended in water for injection (WFI) and treated with 8M Urea to lyse the cells and liberate the FIM2/3 for analysis by ELISA.

Figure 2B:
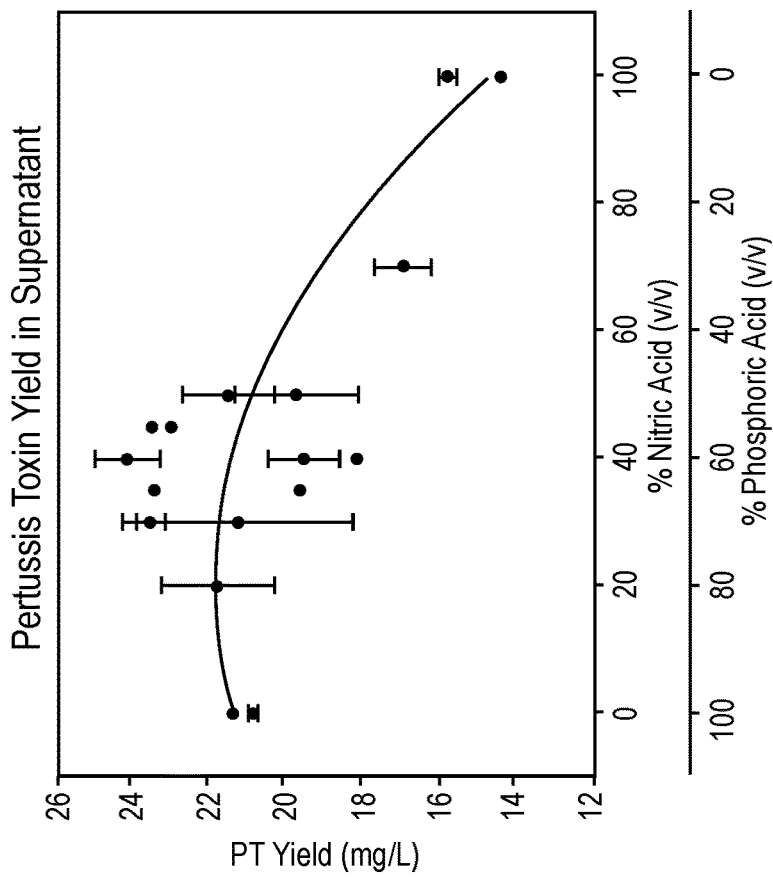
FIGS. 2A-2D depict the effect of using blends of 3.5 M nitric acid and 2.5 M phosphoric acid at different ratios for pH control during *Bordetella* cultivation in complex medium on the yields of PRN (FIG. 2A), PT (FIG. 2B) and FHA (FIG. 2C) from supernatants and FIM2/3 from cellular fractions and supernatants (FIG. 2D) as described in Example 2.
Figure 2A:
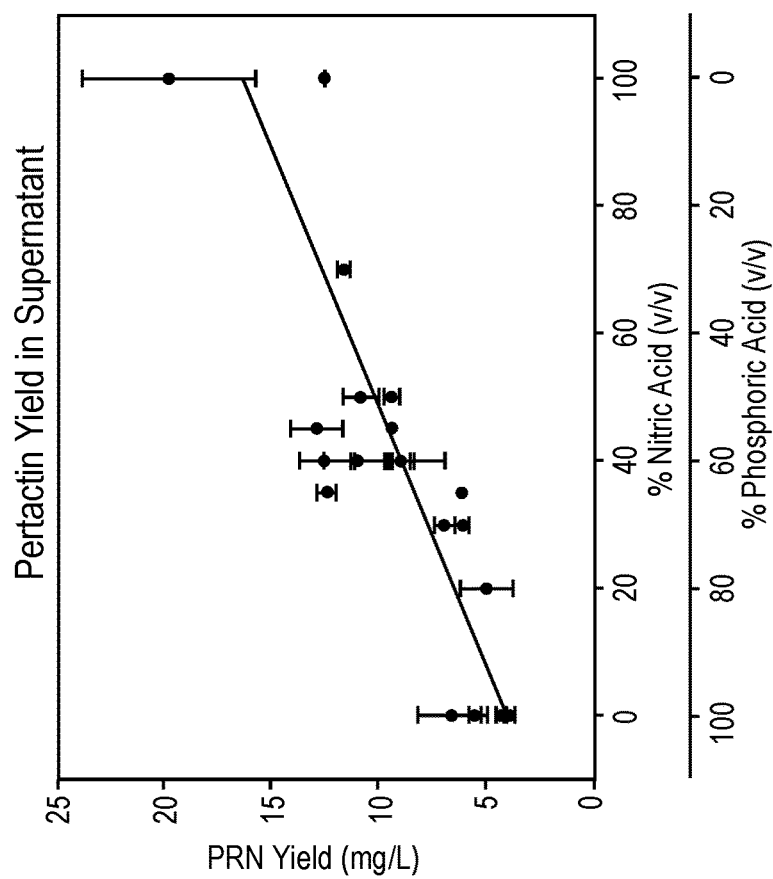
Figure 2D:
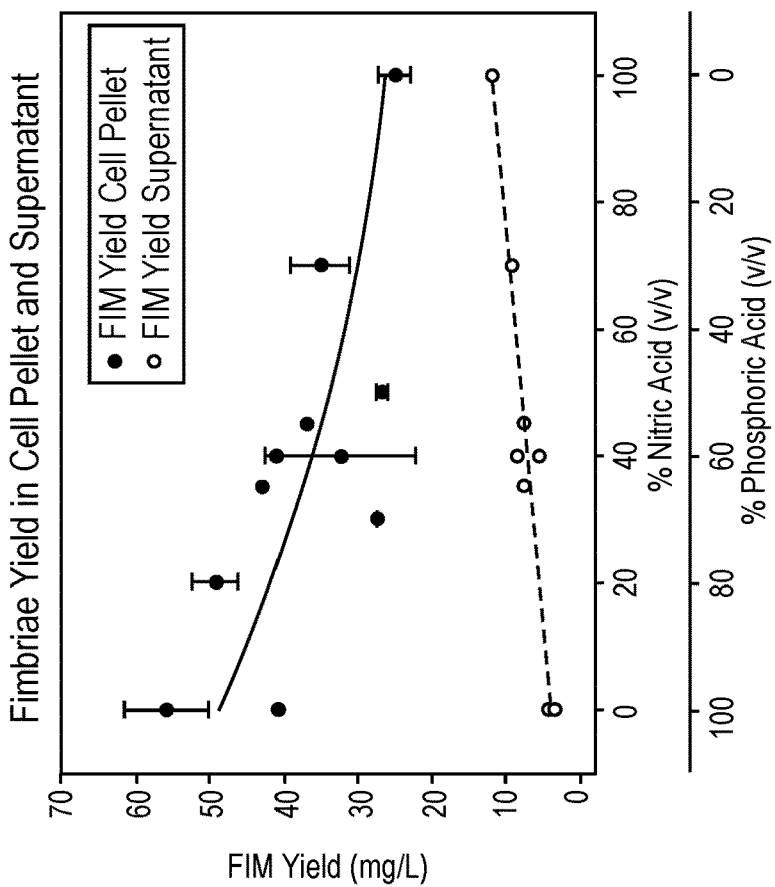
Figure 2C:
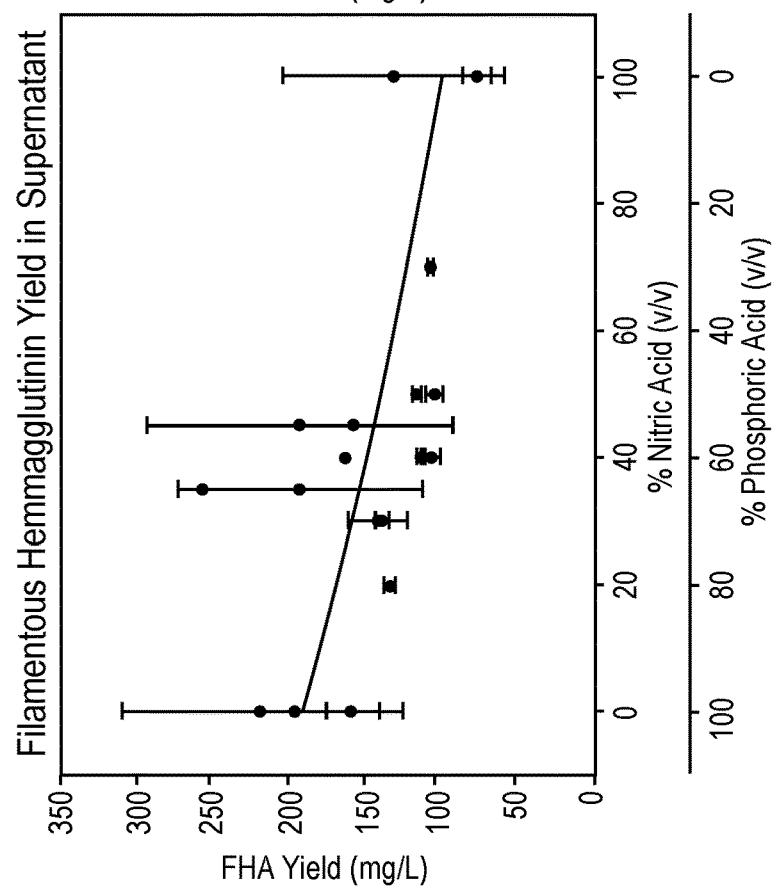
Figure 3B:
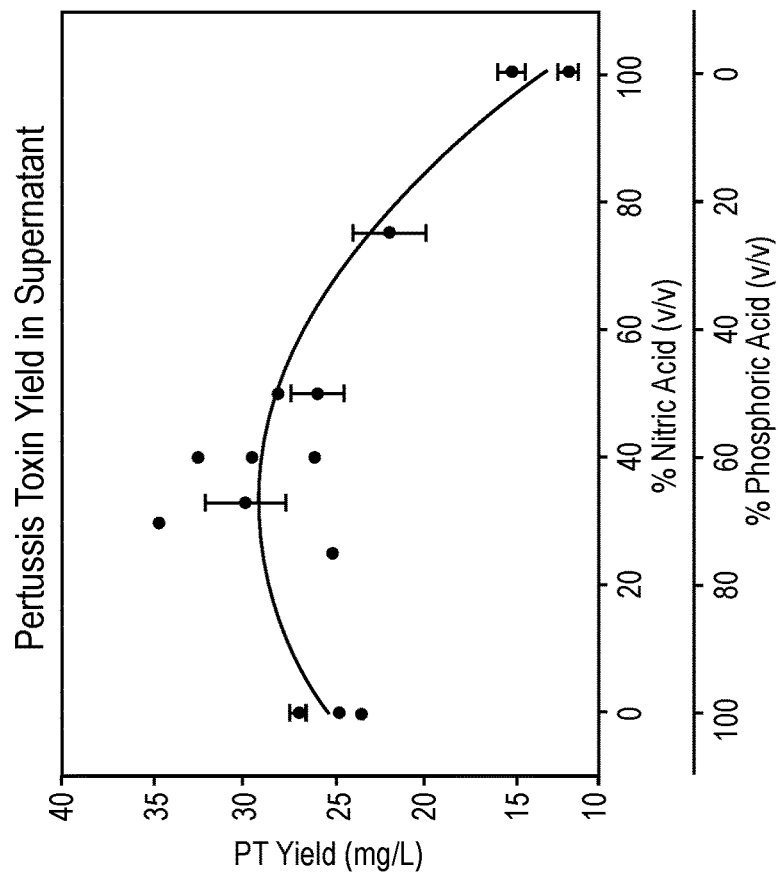
FIGS. 3A-3D depict the effect of using blends of 3.5 M nitric and 2.5 M phosphoric acid at different ratios for pH control during *Bordetella* cultivation in chemically defined medium on the yields of PRN (FIG. 3A), PT (FIG. 3B) and FHA (FIG. 3C) from supernatants and FIM2/3 from cellular fractions and supernatants (FIG. 3D) as described in Example 3.
Figure 3A:
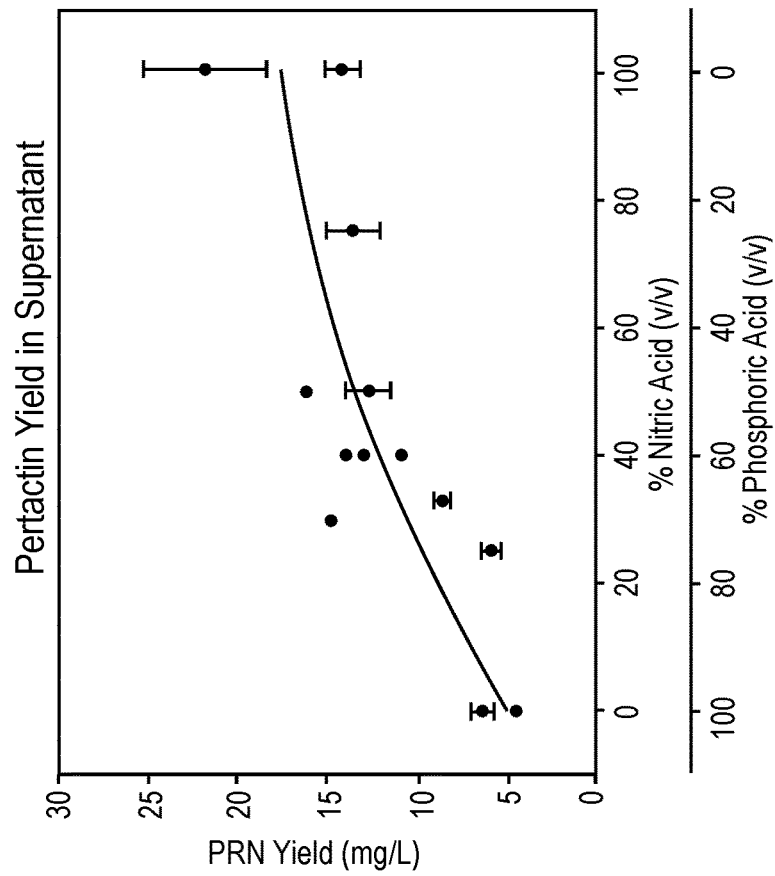
Figure 3D:
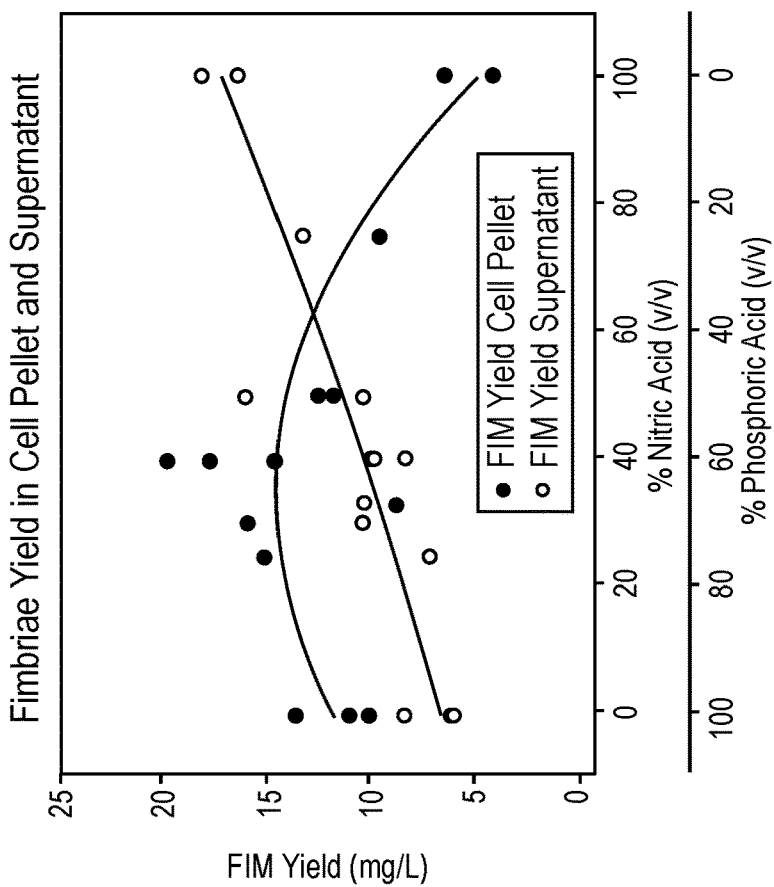
Figure 3C:
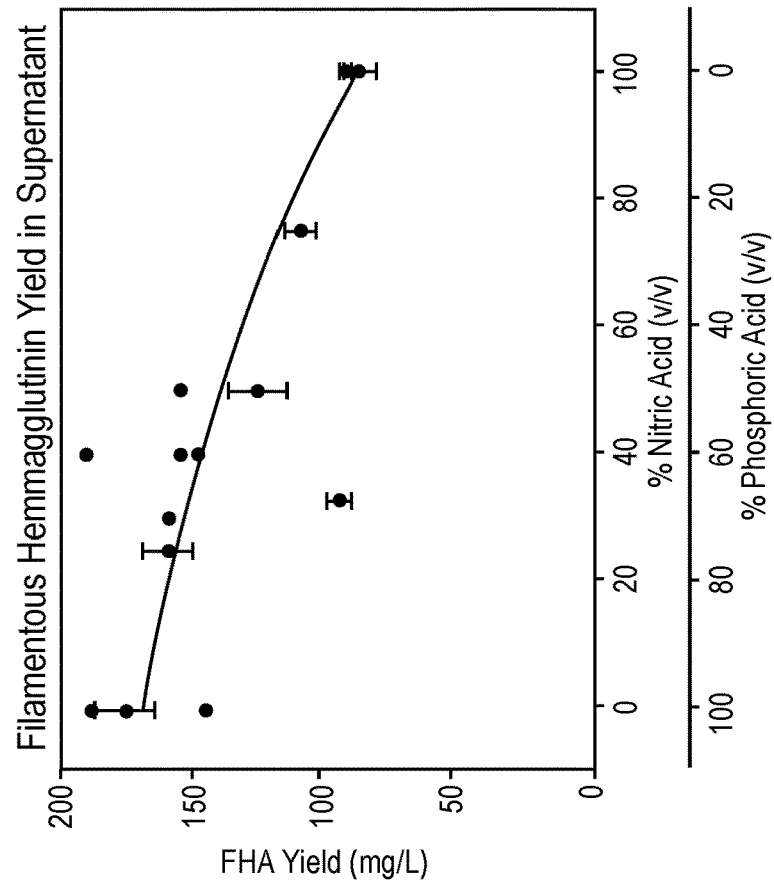
Figure 4B:
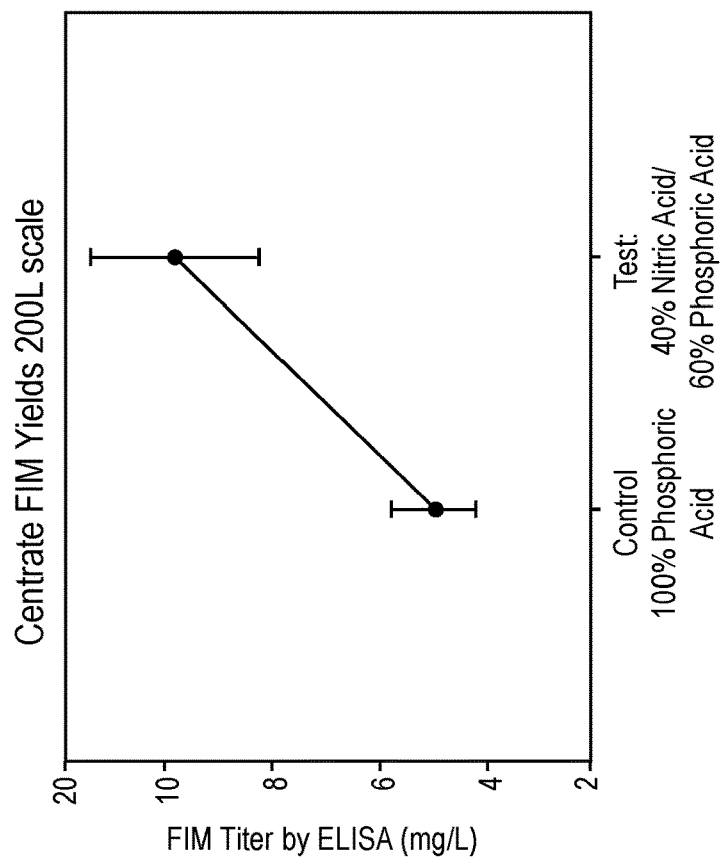
FIGS. 4A-B depict the effect of using blends of 3.5 M nitric and 2.5 M phosphoric acid at different ratios for pH control during *Bordetella* cultivation in complex medium on the yields of PRN from supernatants at 20 L and 200 L scales (FIG. 4A), and FIM2/3 from supernatants (centrate) at 200 L scale (FIG. 4B) as described in Example 4.
Figure 4A:
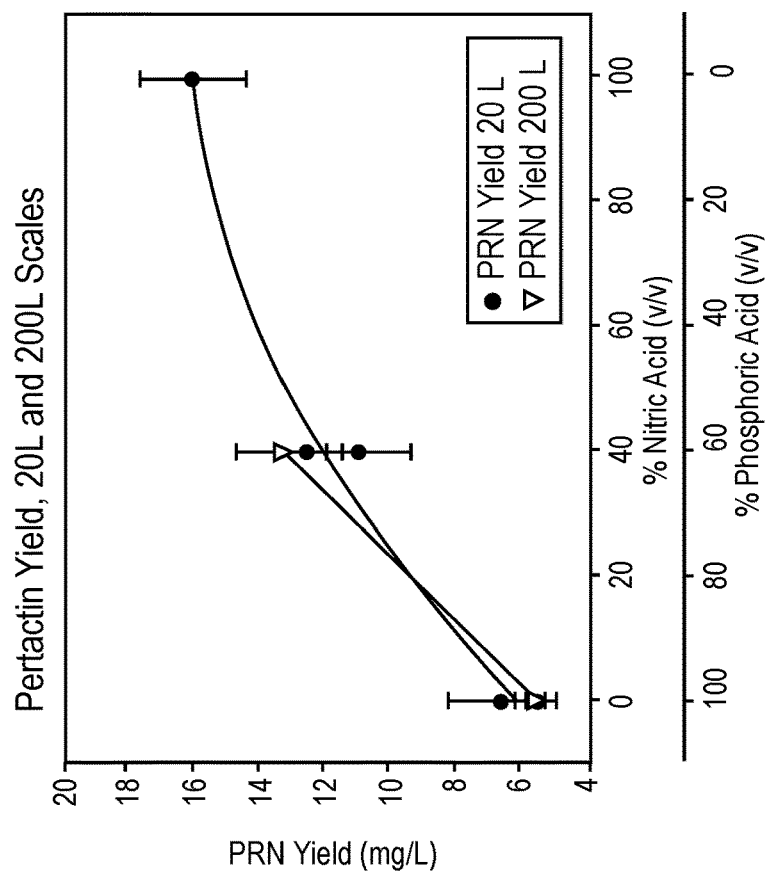

FIGS. 2A-2D show the yield of each antigen as measured by ELISA in the bioreactor harvest for multiple bioreactor runs. FIG. 2A confirms that PRN yield in the supernatant of the bioreactor harvest is increased (4 mg/L to 12-20 mg/L) when a solution comprising 100% 3.5 M nitric acid is used in place of a solution comprising 2.5 M phosphoric acid for pH control. FIG. 2D also demonstrates that FIM2/3 yields in the supernatant were significantly increased from approximately 4 mg/L to 12 mg/L when 100% 3.5 M nitric acid was used instead of 100% 2.5 M phosphoric acid.

FIG. 2D also shows, however, that when a solution comprising 100% 3.5 M nitric acid was used for pH control instead of a solution comprising 100% 2.5 M phosphoric acid, a decrease in FIM2/3 in the cellular fraction was observed (about 50% reduction). Additionally 2b-c also shows that PT and FHA yields in the supernatant of the bioreactor harvest were also significantly reduced with 100% 3.5 M nitric, i.e., 21 mg/L to 15 mg/L and 190 mg/L to 80-120 mg/L, respectively.

As the ratio of nitric acid in the blend used for bioreactor pH control was lowered, however, the decrease in the yield for PT and FHA in the supernatant fraction and FIM2/3 in the cellular fraction was mitigated. See FIGS. 2B-D. Further, at 30-50% 3.5 M nitric acid and 70%-50% 2.5 M phosphoric acid, the improvements to PRN and FIM2/3 yields in the supernatant fraction of the bioreactor harvest were still observed in comparison to the yield when a solution comprising only 100% 2.5 M phosphoric acid was used for pH control (FIGS. 2A and 2D, 7-10 mg/L and 5-9 mg/L, respectively).

Example 3. Acid Blends and Chemically Defined Medium Further Increase PRN and FIM2/3 Yield in Supernatant from *Bordetella* Culture while Mitigating PT and FHA Loss Cultures were also prepared as described above for Example 1, except that a chemically defined medium was used in place of the complex medium. Blends of nitric acid and phosphoric acid at different ratios as described in Example 2 were used for bioreactor pH control. PRN, PT, FHA and FIM2/3 antigens were isolated as described above for Example 2.

FIG. 3 shows the yield of each antigen as measured by ELISA in the bioreactor harvest for multiple bioreactor runs. FIGS. 3A-D also confirm that the PRN yield in the supernatant fraction of the bioreactor harvest is increased (5-7 mg/L to 14-22 mg/L) when 100% 3.5 M nitric acid is used for pH control in place of 100% 2.5 M phosphoric acid. In addition, FIG. 3 also confirms that FIM2/3 yields in the supernatant fraction are significantly increased from approximately 4 mg/L to 16 mg/L when solutions comprising 100% 3.5 M nitric acid are used for pH control instead of solutions comprising 100% 2.5 M phosphoric acid.

In addition, FIG. 3 confirmed a decrease in the FIM2/3 associated with the cellular fraction when 100% 3.5 M nitric acid solution versus 100% 2.5 M phosphoric acid was used for pH control (from 10-14 mg/L to 3-6 mg/L). As similarly shown in Example 2, PT and FHA yields in the supernatant fraction of the bioreactor harvest were also significantly reduced from approximately 24-27 mg/L to 12-15 mg/L and 145-280 mg/L to 85-190 mg/L, respectively, with 100% 3.5 M nitric acid.

As the ratio of nitric acid in the blend used for bioreactor pH control was lowered, however, the decrease in the harvest yields for PT and FHA in the supernatant fraction and FIM2/3 in the cellular fraction was mitigated. See FIGS. 3B-D. Further, at 30-50% 3.5 M nitric acid and 70%-50% 2.5 M phosphoric acid, the improvements to PRN and FIM2/3 yields in the supernatant fraction of the bioreactor harvest were still observed in comparison to the yield when a solution comprising only 100% 2.5 M phosphoric acid was used for pH control (FIGS. 3A and 3D, 10-15 mg/L and 8-12 mg/L, respectively).

Example 4. Acid Blends Increase PRN and FIM2/3 Yield in Supernatant from *Bordetella* Culture at Larger Scales To ensure that the effect of blends of nitric acid and phosphoric acid were not an artifact of small-sale cultivation, experiments were conducted at both the 20 L and 200 L bioreactor scales. At the 20 L scale, seed propagation was initiated in 500 mL shaker flasks containing 100 mL of modified Stainer-Scholte medium (Table 3) supplemented with 100× growth factor solution (Table 4) and cultivated for 44 hours. This primary flask was used to inoculate 4 2 L flasks containing 500 mL of modified Stainer-Scholte medium (Table 3) supplemented with 100× growth factor solution (Table 4) and cultivated for 44 hours. These secondary flasks were used to inoculate 20 L BIOSTAT® Cplus bioreactors (Sartorius Stedium, Bohemia, NY, USA) containing 11.5 L of modified Stainer-Scholte medium (Table 3) supplemented with 100× growth factor solution (Table 4). The first phase is done in a shake flask. A relatively small seed culture is first grown by inoculation from a stock culture (e.g., working seed) and this is grown and used to inoculate a culture (e.g., seed culture, fermentation culture).

All cultivation parameters were controlled in a similar manner and using the same reagents as for the 2 L flasks except that antifoam reagent was used at a higher concentration. In the 20 L bioreactor runs pH was controlled using solutions containing either 0, 40%, and 100% (v/v) 3.5 M nitric acid with the remainder 2.5 M phosphoric acid.

At the 200 L scale, seed propagation was initiated in a 250 mL shaker flask using 100 mL of modified Stainer-Scholte medium (Table 3) supplemented with 100× growth factor solution (Table 4). This primary flask was used to inoculate 4 L flasks containing 1 L of modified Stainer-Scholte medium (Table 3) supplemented with 100× growth factor solution (Table 4), followed by passages in 20 L and 200 L bioreactors. The working volume of the 200 L bioreactor is 160 L. All cultivation parameters were controlled in a similar manner and using the same reagents as for the 2 L flasks except that antifoam reagent was used at a higher concentration. In the 200 L bioreactor runs pH was controlled using solutions containing either 0 and 40% (v/v) 7 M nitric acid with the remainder 5 M phosphoric acid.

FIG. 4A shows that the yield of PRN in the harvest supernatant increases with increasing ratios of nitric acid used for pH control at both the 20 L and 200 L scales in a similar manner to results generated at the 2 L scales. In these experiments at the 20 L and 200 L scales, PRN yields were 5-7 mg/L when 100% 2.5 M and 5 M phosphoric acid was used for pH control, increasing to 11-13 mg/L when 40% (v/v) 3.5 M and 7 M nitric acid was blended with the remainder 2.5 m and 5 M phosphoric acid respectively and used for pH control, and increasing to 16 mg/L when 100% 3.5 M nitric acid was used at the 20 L scale for pH control.

In addition, FIG. 4B confirmed an increase in the FIM2/3 in the supernatant of the 200 L harvest when 40% (v/v) 7 M nitric acid with the remainder 5 M phosphoric acid versus 100% 2.5 M phosphoric acid was used for pH control (9.9 mg/L versus 5.0 mg/L).

PRN was also purified from the harvested supernatant at both the 20 L and 200 L scales using bioreactor, primary recovery and purification processes that were scaled-down from a 2000 L manufacturing process and characterized using different analytical methods. The summary in Table 6 for the 20 L material shows that the quality of the purified PRN when characterized using a variety of different analytical methods was not substantially different when an acid blend (40% nitric acid/60% phosphoric acid) was used when compared to both PRN from control runs (100% 2.5 M phosphoric acid) at the same scale or PRN produced using a 2000 L manufacturing process (which also uses 100% 2.5 M phosphoric acid for pH control).

TABLE 6

Characterization of purified PRN from a 20 L bioreactor processes using 100% 2.5M phosphoric acid (control) and an acid blend (40% nitric acid/60% phosphoric acid) for bioreactor pH control compared to purified material from a 2,000 L manufacturing process (IO lots).

| Test | Result |
|---|---|
| Pertussis Toxin (CHO) | Nitric/Phosphoric acid blend lots similar to control and IO lots |
| SDS-PAGE Purity | Nitric acid/Phosphoric blend lots similar to control and IO lots |
| Residual Tracheal Cytotoxin<br>Residual Adenylate Cyclase Toxin<br>Residual Dermonecrotic Toxin | Nitric/Phosphoric acid blend lots similar to control and IO lots |
| Differential Scanning Calorimetry | Nitric/Phosphoric acid blend lots similar to control and IO lots |
| Circular Dichroism | Nitric/Phosphoric acid blend lots similar to control and IO lots |
| Host cell Protein Analysis (MS) | Nitric/Phosphoric acid blend lots similar to control and IO lots |
| Intact Mass (Mass Spectrometry) | Intact and truncated PRN in control and nitric/phosphoric acid blend lots |

TABLE 6-continued Characterization of purified PRN from a 20 L bioreactor processes using 100% 2.5M phosphoric acid (control) and an acid blend (40% nitric acid/60% phosphoric acid) for bioreactor pH control compared to purified material from a 2,000 L manufacturing process (IO lots).

| Test | Result |
|---|---|
| Strong Anion Exchange HPLC | Nitric/Phosphoric acid blend lots similar to control and IO lots |

While one or more exemplary embodiments have been described in the specification, it will be understood by those of ordinary skill in the art that various changes in form and details may be made therein without departing from the spirit and scope of the inventive concept as defined by the following claims.

What is claimed is:

1. A method for cultivating a species of *Bordetella*, which method comprises:
cultivating a *Bordetella* species under aerobic conditions in a liquid culture medium; and
maintaining a pH of the liquid culture medium during cultivation of said species, wherein maintaining the pH of the liquid culture medium comprises:
adding a first and second acid to the liquid culture medium to maintain the pH of the liquid culture medium within a predetermined range of pH values during cultivation of said *Bordetella* species, wherein said first acid is nitric acid, hydrochloric acid or sulfuric acid and said second acid is phosphoric acid.

2. The method of claim 1, wherein the first acid and the second acid are combined in a solution, said solution comprising about 30% to about 50% of the first acid and about 50% to about 70% of the second acid (v/v).

3. The method of claim 1, wherein the first acid and the second acid are combined in a solution, said solution comprising about 40% of the first acid and about 60% of the second acid (v/v).

4. The method of claim 1, wherein the first acid is nitric acid and the second acid is phosphoric acid.

5. The method of claim 1, wherein said method further comprises isolating *Bordetella* antigens from the liquid culture medium.

6. The method of claim 5, wherein isolating *Bordetella* antigens comprises:
separating the liquid culture medium after cultivation of *Bordetella* into a cellular fraction and a supernatant fraction;
isolating one or more of Pertussis Toxin (PT), Filamentous Haemagglutinin (FHA) and pertactin (PRN) from the supernatant fraction, and
isolating Fimbriae Types 2 and 3 from the cellular fraction.

7. The method of claim 6, wherein said method further comprises formulating the isolated antigens as a subunit vaccine.

8. The method of claim 1, wherein said *Bordetella* species is *Bordetella pertussis*.

9. The method of claim 1, wherein said predetermined range of pH values is from about 6.0 to about 9.0.

10. The method of claim 1, wherein said predetermined range of pH values is from about 6.8 to about 7.3.

11. The method of claim 1, wherein said cultivation of said *Bordetella* species occurs under large-scale production conditions.

12. The method of claim 1, wherein the liquid culture medium is a chemically defined liquid culture medium.

13. The method of claim 12, wherein said chemically defined liquid culture medium is a Stainer-Scholte medium supplemented with dimethyl-P-cyclodextrin.

14. A method for cultivating a *Bordetella* species, which method comprises:
cultivating a *Bordetella* species under aerobic conditions in a liquid culture medium; and maintaining a pH of the liquid culture medium during cultivation of said species, wherein maintaining the pH of the liquid culture medium comprises:
adding nitric acid to the liquid culture medium to maintain the pH of the liquid culture medium within a predetermined range of pH values during cultivation of said *Bordetella* species.

15. The method of claim 14, wherein said method further comprises isolating *Bordetella* antigens from the liquid culture medium.

16. The method of claim 15, wherein isolating *Bordetella* antigens comprises:
separating the liquid culture medium after cultivation of *Bordetella* into a cellular fraction and a supernatant fraction;
isolating *Bordetella* antigens from the supernatant fraction, wherein the isolated *Bordetella* antigens comprise pertactin.

17. The method of claim 15, wherein said method further comprises formulating the isolated *Bordetella* antigens as a subunit vaccine.

* * * * *

UNITED STATES PATENT AND TRADEMARK OFFICE
CERTIFICATE OF CORRECTION

Page 1 of 1

PATENT NO. : 11,970,690 B2
APPLICATION NO. : 16/981200
DATED : April 30, 2024
INVENTOR(S) : Patrick Farrell et al.

It is certified that error appears in the above-identified patent and that said Letters Patent is hereby corrected as shown below:

In the Claims

At Column 22, Line 23: "dimethyl-P-cyclodextrin" should be "dimethyl-β-cyclodextrin".

Signed and Sealed this
Twenty-second Day of October, 2024

Katherine Kelly Vidal
*Director of the United States Patent and Trademark Office*